US012622600B2

(12) United States Patent
Patrick et al.

(10) Patent No.: US 12,622,600 B2
(45) Date of Patent: May 12, 2026

(54) SYSTEM AND METHOD FOR MAINSTREAM EXHALED OXYGEN SENSOR

(71) Applicant: The Trustees of Princeton University, Princeton, NJ (US)

(72) Inventors: Charles L. Patrick, Princeton, NJ (US); Jonas Westberg, Princeton, NJ (US); Gerard Wysocki, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 1221 days.

(21) Appl. No.: 17/609,057

(22) PCT Filed: May 6, 2020

(86) PCT No.: PCT/US2020/031652
§ 371 (c)(1),
(2) Date: Nov. 5, 2021

(87) PCT Pub. No.: WO2020/227394
PCT Pub. Date: Nov. 12, 2020

(65) Prior Publication Data
US 2022/0233097 A1 Jul. 28, 2022

Related U.S. Application Data

(60) Provisional application No. 62/844,306, filed on May 7, 2019.

(51) Int. Cl.
*A61B 5/083* (2006.01)
*A61B 5/00* (2006.01)
*G01N 21/61* (2006.01)
*G01N 33/00* (2006.01)

(52) U.S. Cl.
CPC .......... *A61B 5/0833* (2013.01); *A61B 5/0075* (2013.01); *G01N 21/61* (2013.01); *G01N 33/0036* (2013.01)

(58) Field of Classification Search
None
See application file for complete search history.

(56) References Cited

U.S. PATENT DOCUMENTS

| | | |
|---|---|---|
| 3,516,744 A | 6/1970 | Hinman et al. |
| 3,676,003 A | 7/1972 | Naiman et al. |
| (Continued) | | |

FOREIGN PATENT DOCUMENTS

WO        9000732 A1      1/1990

OTHER PUBLICATIONS

Extended European Search Report for corresponding European Application No. 20802811.8, dated Oct. 2, 2023.
(Continued)

*Primary Examiner* — Jay B Shah
(74) *Attorney, Agent, or Firm* — MEAGHER EMANUEL LAKS GOLDBERG & LIAO, LLP

(57)        ABSTRACT

According to various embodiments, a sensing device for measuring oxygen concentration cycles in breath is disclosed. The sensing device includes a laser configured to emit light at an A-band of oxygen, a lens configured to collimate the light, and a multi-pass cell configured to contain a replaceable sample cell. The light passes through the multi-pass cell and is attenuated by oxygen in the sample cell. The sensing device further includes a photodetector configurated to convert the attenuated light into an electrical signal, and a lock-in amplifier or an equivalent processing circuit configured to determine oxygen concentration from the electrical signal.

10 Claims, 8 Drawing Sheets

(56)                 References Cited

U.S. PATENT DOCUMENTS

| | | | |
|---|---|---|---|
| 5,570,697 | A | 11/1996 | Walker et al. |
| 5,572,031 | A | 11/1996 | Cooper et al. |
| 6,356,350 | B1 | 3/2002 | Silver et al. |
| 2009/0024014 | A1 | 1/2009 | Sugo et al. |
| 2011/0194577 | A1 | 8/2011 | Wells et al. |
| 2014/0293283 | A1* | 10/2014 | Farooq ................... G01N 21/61 |
| | | | 356/437 |
| 2018/0239430 | A1 | 8/2018 | Tadi et al. |
| 2018/0356266 | A1* | 12/2018 | Robbins ................. G01N 21/39 |

OTHER PUBLICATIONS

Patrick, Link et al., "Time-resolved oxygen monitoring in human breath," 2019 Conference on Lasers and Electro-Optics (CLEO), OSA, May 5, 2019.

International Search Report and Written Opinion for corresponding PCT Application No. PCT/US2020/031652, dated Aug. 4, 2020.
Robinson et al., "Consensus statement for inert gas washout measurement using multiple- and single-breath tests", Eur. Respir. J. vol., 41, pp. 507-522, 2013.
Ciaffoni et al., "In-airway molecular flow sensing: A new technology for continuous, noninvasive monitoring of oxygen consumption in critical care", Sci. Adv. 2, e1600560, pp. 1-9, Aug. 10, 2016.
Hodgkinson et al., "Optical gas sensing: a review", Meas. Sci. Technol., vol. 24, Jan. 2004, pp. 1-59, 2013.
Westberg et al., "Faraday Modulation Spectroscopy: Theoretical Description and Experimental Realization for Detection of Nitric Oxide", Umea University, 2013.
Brumfield et al., "Faraday rotation spectroscopy based on permanent magnets for sensitive detection of oxygen at atmospheric conditions", Opt. Express 29727, vol. 20, No. 8, Dec. 31, 2012.

* cited by examiner

Time(s)

SYSTEM AND METHOD FOR MAINSTREAM EXHALED OXYGEN SENSOR

CROSS-REFERENCE TO RELATED APPLICATIONS

This application claims priority to provisional application 62/844,306, filed May 7, 2019, which is herein incorporated by reference in its entirety.

FIELD OF THE INVENTION

The present invention relates generally to measuring oxygen and, more particularly, to a system and method to measure oxygen concentration cycles in breath for health monitoring.

BACKGROUND OF THE INVENTION

Monitoring of the rate of oxygen consumption in critical care patients provides unique insight into metabolic function and may therefore be of use in a variety of clinical settings. However, time-resolved and accurate sampling of the human breath cycle with a desired accuracy of <1% of $O_2$ and a sampling rate of 100 Hz places high demands on the oxygen sensor. So far, commercially available techniques for oxygen monitoring in breath are either bulky, limited in accuracy, or have slow response times.

Many of these issues can be effectively addressed by the recent advances of laser spectroscopy, whose strengths are high temporal resolution, selectiveness, and sensitivity, all provided in a non-invasive manner. However, the small absorption cross-sections of $O_2$ is often compensated with long absorption pathlengths or other optical enhancement techniques to reach the desired minimum detection limits (MDL), which often lead to bulky sensors with large sampling volumes undesired for routine mainstream breath monitoring.

The ideal form factor for the oxygen sensor is similar to conventional capnography instruments that are routinely used for monitoring breath via airflow rate and $CO_2$ concentration measurements. Providing an oxygen sensing platform as a complement to the established $CO_2$ sensors will further expand the routine breath analysis applications by enabling collection of additional metabolic function data.

Hospital rooms are fitted with many vital sign monitors: heart rate, blood pressure, body temperature, etc. However, the rate of oxygen consumption while breathing is not measured routinely. Monitoring of the rate of oxygen consumption of patients in critical care provides insight into the metabolic function of the patients which is useful in several clinical dilemmas: neo-natal complications, sepsis identification, hypoxia detection, and nonresponsive patient monitoring.

Real time breath measurement must be accurate and precise in order to clearly resolve the cycles within each breath that are indicative of various ailments. Devices used in medical settings must also be user friendly, robust, and compact. Devices must also utilize a sterilized replaceable adapter.

As such, there is a need for an oxygen sensor based on laser spectroscopy that addresses the above requirements.

SUMMARY OF THE INVENTION

According to various embodiments, a sensing device for measuring oxygen concentration cycles in breath is disclosed. The sensing device includes a laser configured to emit light at an A-band of oxygen, a lens configured to collimate the light, and a multi-pass cell configured to contain a replaceable sample cell. The light passes through the multi-pass cell and is attenuated by oxygen in the sample cell. The sensing device further includes a photodetector configured to convert the attenuated light into an electrical signal, and a lock-in amplifier configured to determine oxygen concentration from the electrical signal.

According to various embodiments, a sensing device for measuring oxygen concentration cycles in breath is disclosed. The sensing device includes a laser configured to emit light at an A-band of oxygen, a lens configured to collimate the light, and a multi-pass cell configured to contain a replaceable sample cell. The light passes through the multi-pass cell and is attenuated by oxygen in the sample cell. The sample cell includes a first window between the lens and multi-pass cell and a second window between the multi-pass cell and photodetector. The sensing device further includes a photodetector configured to convert the attenuated light into an electrical signal, and a lock-in amplifier configured to determine oxygen concentration from the electrical signal.

According to various embodiments, a sensing device for measuring oxygen concentration cycles in breath is disclosed. The sensing device includes a laser configured to emit light at an A-band of oxygen, a lens configured to collimate the light, and a multi-pass cell configured to contain a replaceable sample cell. The light passes through the multi-pass cell and is attenuated by oxygen in the sample cell. The sensing device further includes a photodetector configured to convert the attenuated light into an electrical signal, and a processing circuit configured to determine oxygen concentration from the electrical signal.

Various other features and advantages will be made apparent from the following detailed description and the drawings.

BRIEF DESCRIPTION OF THE DRAWINGS

In order for the advantages of the invention to be readily understood, a more particular description of the invention briefly described above will be rendered by reference to specific embodiments that are illustrated in the appended drawings. Understanding that these drawings depict only exemplary embodiments of the invention and are not, therefore, to be considered to be limiting its scope, the invention will be described and explained with additional specificity and detail through the use of the accompanying drawings, in which.

DETAILED DESCRIPTION OF THE INVENTION

Generally disclosed herein are embodiments for a system and method for a novel, small, and lightweight sensor for continuous in-airway monitoring of oxygen at a high sampling rate (100 Hz). A prototype sensor head has dimensions of <80×40×40 mm and weighs less than 200 g. The system uses a short optical pathlength directly probing the exhaled air in a mainstream or sidestream configuration. The sensor can be used as a stand-alone sensor or in conjunction with capnographic systems from leading medical equipment manufacturers. The target metrics are a measurement precision of <0.5% $O_2$ with a temporal resolution of 10 ms (100 Hz sampling rate), which is adequate to fully resolve the oxygen concentration within a single breath cycle.

Figure 1:
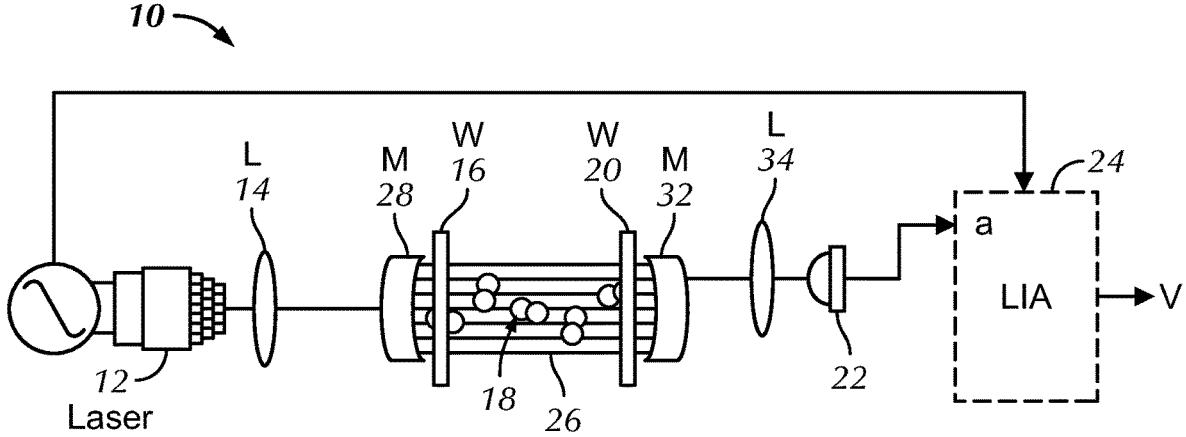
FIG. 1 depicts a block diagram of an $O_2$ sensor according to an embodiment of the present invention.

FIG. 1 depicts a compact and robust sensor 10 for measuring oxygen concentration cycles in breath for health monitoring according to an embodiment of the present invention. To optically probe the molecular transitions of oxygen, the sensor 10 uses a distributed feedback (DFB) diode laser 12 emitting light at the A-band of oxygen in a continuous wave mode in a spectral region of 760-765 nm. Any other type of laser 12 operating in this spectral region can be used in this system (e.g. vertical cavity surface emitting lasers (VCSEL), optical fiber lasers, as nonlimiting examples). The laser frequency can be modulated at 3.37 kHz with an optimized modulation depth of 7 GHz (~4 half-widths at half maximum of the target transition).

The laser light is collimated by a single lens 14 and passes through a first anti-reflection (AR) coated window 16 into a sample cell 18 where it is attenuated by oxygen. The lens 14 may be a BK7 aspheric AR coated (650-1050 nm) lens and the first window 16 may be a 100 μm-thick BK7 AR coated (650-1050 nm) window, as nonlimiting examples. The first window 16 (as well as a second window 20) define the interaction volume of the measured breath, protect multipass cell mirrors from elements in the breath (e.g. aerosols, particles, water condensation), and ensure sterility. The windows 16, 20 are an integral part of a replaceable adapter that can either be sterilized or made disposable (to be described further below). Other window materials (such as fused silica, CaF2, Sapphire, quartz, as nonlimiting examples) could be used as long as the attenuation of light in the 760-765 nm wavelength range is low (less than 5%). Also, different thicknesses can be used as long as the beam displacement caused by the windows 16, 20 are properly accounted for and assures reproducible alignment. AR coating is used to lower reflective losses and eliminate unwanted reflections in the system and can alternatively be replaced with windows oriented at a Brewster angle.

The exiting beam from the sample cell 18 passes through the second anti-reflection coated window 20 and is directed onto a photodetector 22, which converts the optical beam to an electrical signal. The photodetector 22 is coupled to a lock-in amplifier (LIA) 24 that demodulates a useful signal at the harmonics of the laser modulation frequency. Any commercially available or self-constructed LIA can be used. Further, a dedicated circuit capable of phase-sensitive detection of modulated signals (e.g. I/Q demodulators, analog-to-digital converters followed by digital signal processing, as nonlimiting examples) or circuits capable of narrow-band filtering of signals at the harmonics of laser modulation frequency can be used to analyze photodetector signals in alternative embodiments.

The sensor 10 uses a 21-pass, miniature Herriott-type multipass cell 26 to increase the interaction length with the sample while keeping the physical dimensions of the sensor head small. The collimated beam is directed into the multi-pass cell 26 through a hole in a first mirror 28. The multi-pass cell chassis provides magnetic attachments and self-positioning for a disposable adapter 30 (for instance, a 3D printed adapter) assuring repeatable alignment. A heating element is placed in contact with the $O_2$ sensor head chassis to prevent condensation on the windows during measurement. The disposable adapter 30 has standardized inlet and outlet outer diameter sizes for breath airway adapters (15 mm and 22 mm) and two 100 μm-thick AR coated (650-1050 nm) BK7 windows 16, 20 placed on the ends of the adapter (~3 cm apart) perpendicular to the airway that allows the laser beam to pass through.

After 21 passes through the airway adapter 30, traveling ~0.6 m through the sample chamber 18, the beam exits through a hole in the second multipass cell mirror 32 and is measured using the photodetector 22 (Thorlabs SM052A) equipped aspheric with a focusing lens 34 (Thorlabs AL1225M-B). The signal from the detector 22 is amplified using a transimpedance amplifier (FEMTO DHPCA-100), whose output is demodulated using the lock-in amplifier 24. The LIA 24 provides access to multiple harmonics of the demodulated signal and the 3$^{rd}$ harmonic is used to lock the laser 12 to the transition and the 2$^{nd}$ and 1$^{st}$ harmonics (2f and 1f respectively) are used to determine the $O_2$ concentration using ratio of the two signals (so called 2f/1f normalization methodology). This system optimization allowed to achieve further improvement of short-term sensitivity down to ~0.04% $O_2$ at 10 ms averaging time.

Figure 2A:
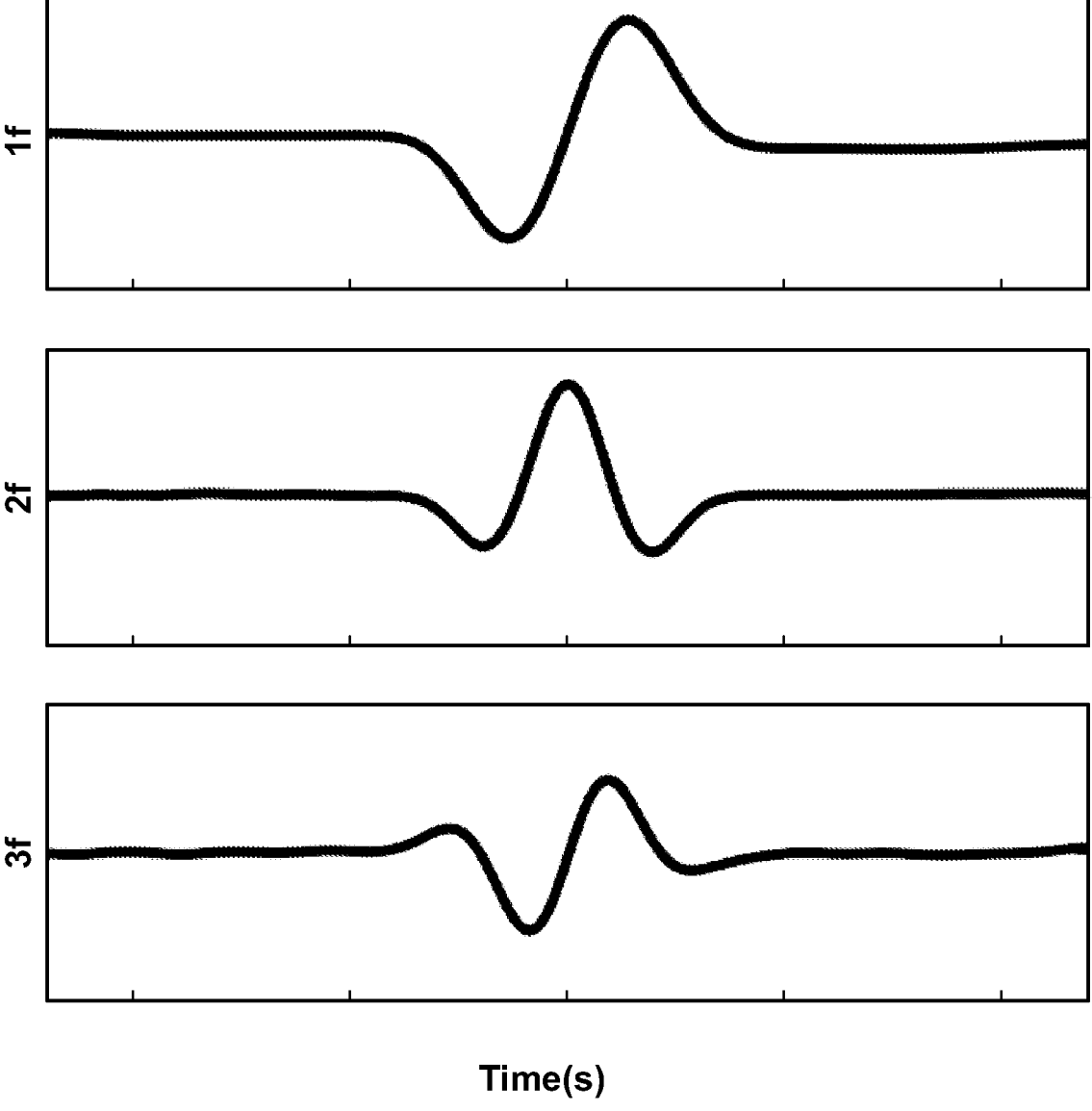
FIG. 2(a) depicts a graph of signal harmonics of a $^PP_5(5)$ transition of oxygen according to an embodiment of the present invention.

Sensitivity of the sensor 10 can be increased by extending the path length with a miniaturized multi-pass cell 26 in the sample cell 18, which also allows for a compact system. The value corresponding to oxygen concentration is extracted from the 2f signal from the LIA 24, shown in FIG. 2(a). The multi-pass cell enables the necessary detection limits. The embodiment shown in FIG. 1 uses wavelength modulation spectroscopy (WMS) based on the LIA 24.

The sample cell 18 in FIG. 1 includes a miniaturized, multi-pass cell 26 that uses two concave mirrors 28, 32 at each end to fold the beam path multiple times, which based on the 762 nm wavelength, leads to an optical path length of about 70 cm with only about 3 cm of mirror separation, effectively increasing the sensitivity by >20 times while keeping the system dimensions to a minimum. Any metallic or dielectric mirrors with sufficient reflectivity in the 760-765 nm wavelength range can be used.

The current of the laser 12 is modulated causing the wavelength of the generated light to be modulated by a modulation depth of 7 GHz (~4 half-widths at half maximum of the target transition). To acquire an optical spectrum the laser current is additionally ramped so that its optical frequency is tuned across the target transition, and the WMS absorption spectrum can be observed using the LIA 24. The LIA 24 gives access to multiple harmonics of the laser modulation frequency. The $3^{rd}$ harmonic does not experience offset due to nonlinearities of the laser current response and is therefore used to lock the optical frequency of the laser 12 to the center of the transition. Meanwhile, the $2^{nd}$ harmonic signal value from the LIA 24 is used to determine the oxygen concentration. The amplitude of the $2^{nd}$ harmonic signal value from the LIA 24 is proportional to oxygen concentration and after calibration (e.g. through a measurement of a known gas concentration i.e. from a calibration gas cylinder) a proportionality coefficient can be recorded and used for oxygen concentration measurements. The $2^{nd}$ harmonic signal value from the LIA 24 is proportional to laser optical power received by the photodetector 22. To mitigate this power dependence, the normalization to the 1st harmonic signal value from the LIA 24 is used. At the center of the transition the 1st harmonic signal has an offset that is proportional to the received laser power, thus via 2f/1f normalization the measured oxygen concentration does not depend on received laser power (i.e. that also suppresses transmission fluctuations due to window fogging).

Figure 3A:
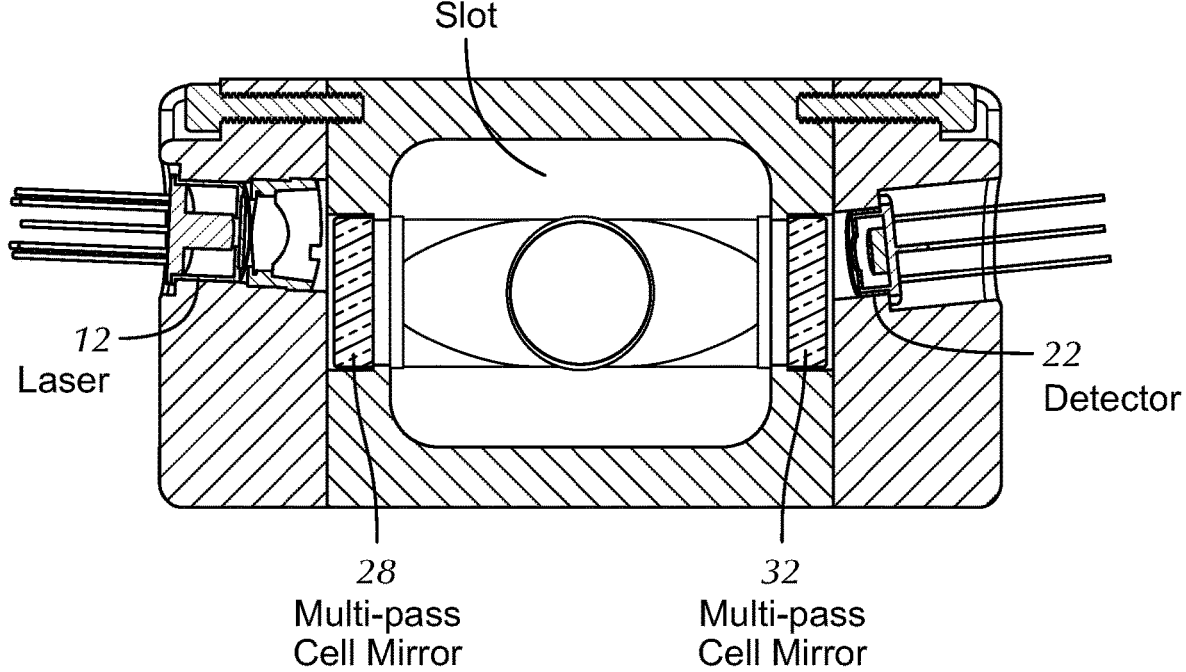
FIG. 3(a) depicts a schematic diagram of an $O_2$ sensor according to an embodiment of the present invention.
Figure 3B:
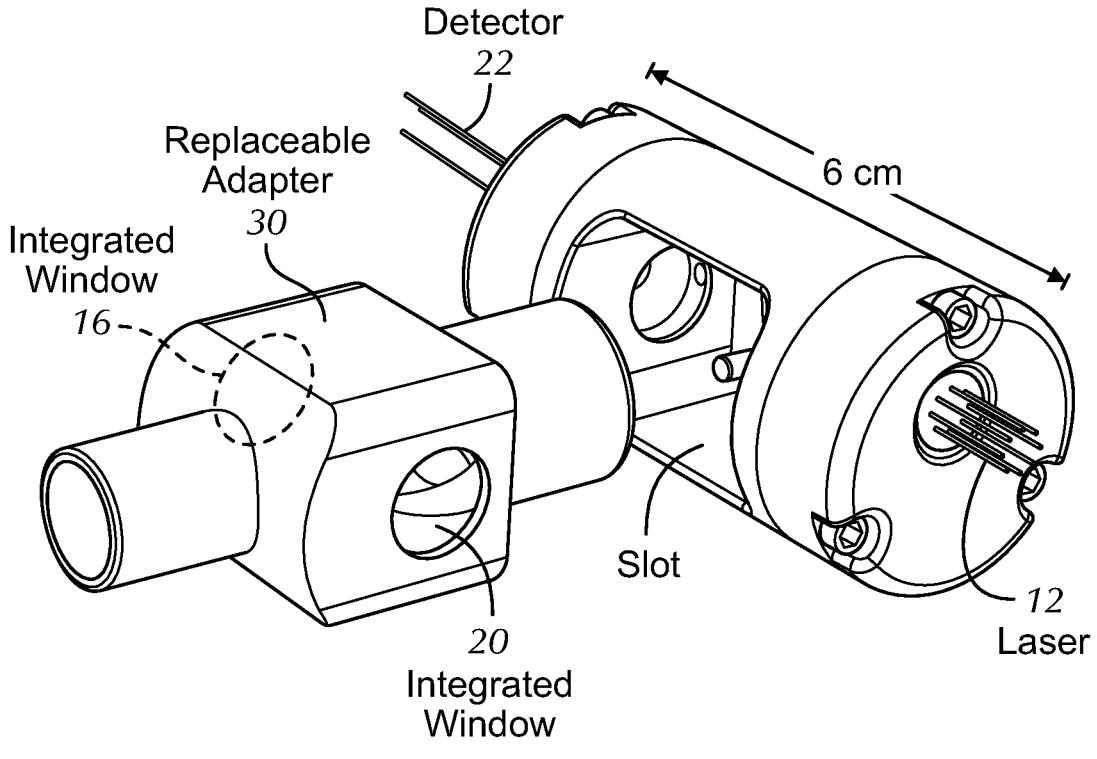
FIG. 3(b) depicts a conceptual drawing of the $O_2$ sensor according to an embodiment of the present invention.
Figure 3B:
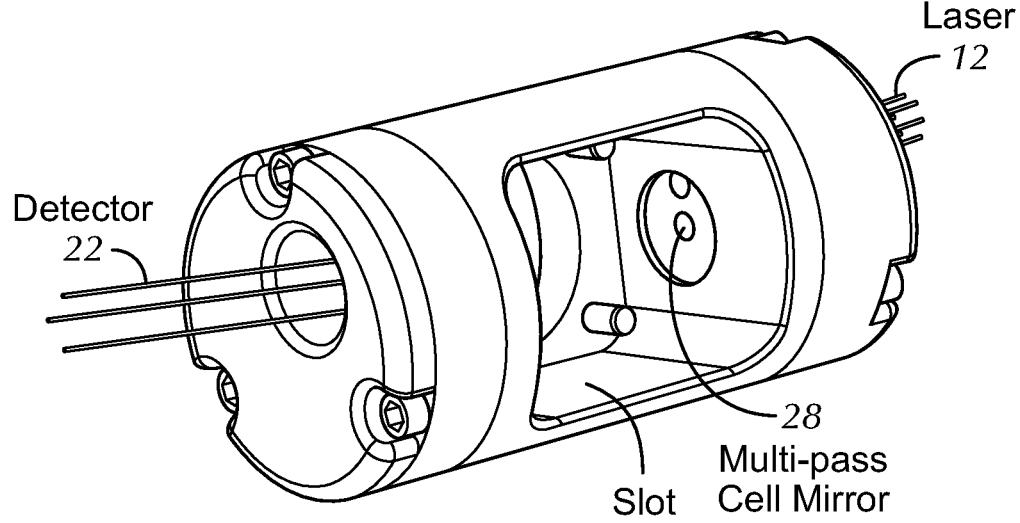

A disposable adapter 30 should be included for medical applications. The chamber that a user's breath flows though must be cheap, as well as easily and robustly replaced on a regular basis by non-technical personnel. It can be standard housing made of aluminum or molded plastic, as nonlimiting examples. FIGS. 3(a)-(b) depicts a schematic overview of the sensor and a conceptual exploded view drawing with the adapter 30.

A removable adapter 30 serves a purpose of a sample cell 18 inserted inside of the multi-pass cell 26 to allow for a disposable piece to be used so that it can be swapped out for different patients. In order to accomplish this task of having a separate sample cell 18 inside a multi-pass cell 26, anti-reflection coated windows 16, 20 are used to reduce reflection losses. However, it is to be noted Brewster angled windows instead of anti-reflection coated mirrors would work as well.

Figure 4A:
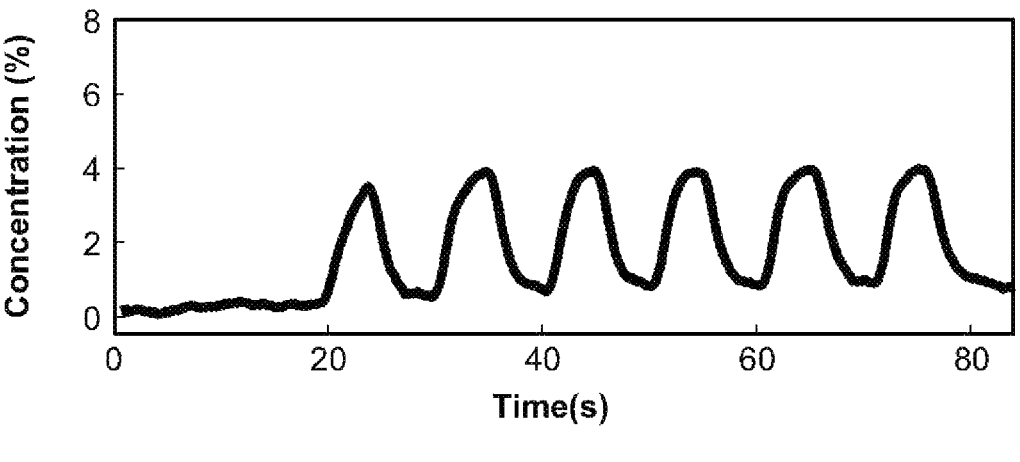
FIG. 4(a) depicts a graph of simulated rapid breathing according to an embodiment of the present invention.
Figure 4B:
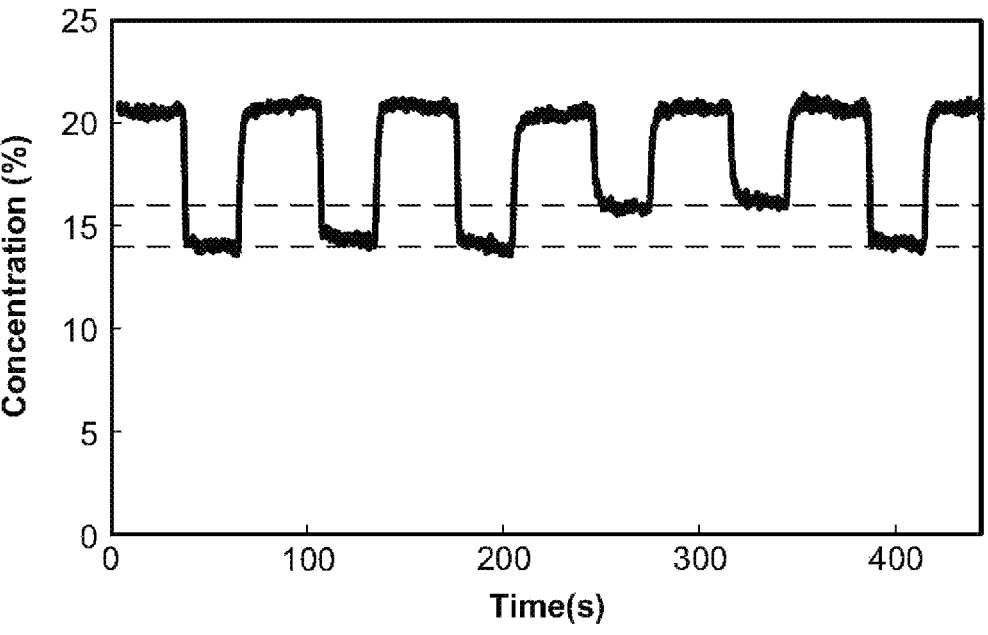
FIG. 4(b) depicts a graph of simulated breathing with 14 and 16 percent according to an embodiment of the present invention.

A prototype embodiment is able to reach target metrics while implementing an easily insertable and removable, disposable sample cell 18. In addition, its small size allows it to be easily transportable. As noted earlier, the schematic overview and conceptual drawing of the sensor 10 for commercialization is shown in FIGS. 3(a)-(b). The prototype was assembled using a machined aluminum chassis and a plastic 3D printed adapter, as shown in FIGS. 3(a)-(b). The final device could be easily manufactured using either a combination of precise machining of metal parts and injection molding of plastic parts or if properly designed, injection molding only could be used if all the parts are designed in moldable plastic materials (provided mechanical stability will be sufficient to maintain optical alignment over extended period of time). This embodiment fixes the laser 12 and detector 22 to the assembly so that it can be implemented into a compact assembly. Using this device 10, several measurements are shown in FIGS. 4(a)-(b). Fast shallow breaths are simulated using an Environics 4040 gas mixture and measured with the sensor 10 in FIG. 4(a). In FIG. 4(b), the gas mixture is again used to simulate breathing, but on the $4^{th}$ and $5^{th}$ "breath," the concentration is changed to 16% instead of 14% to emphasize the difference that is of interest for the relation to metabolic function.

Figure 5:
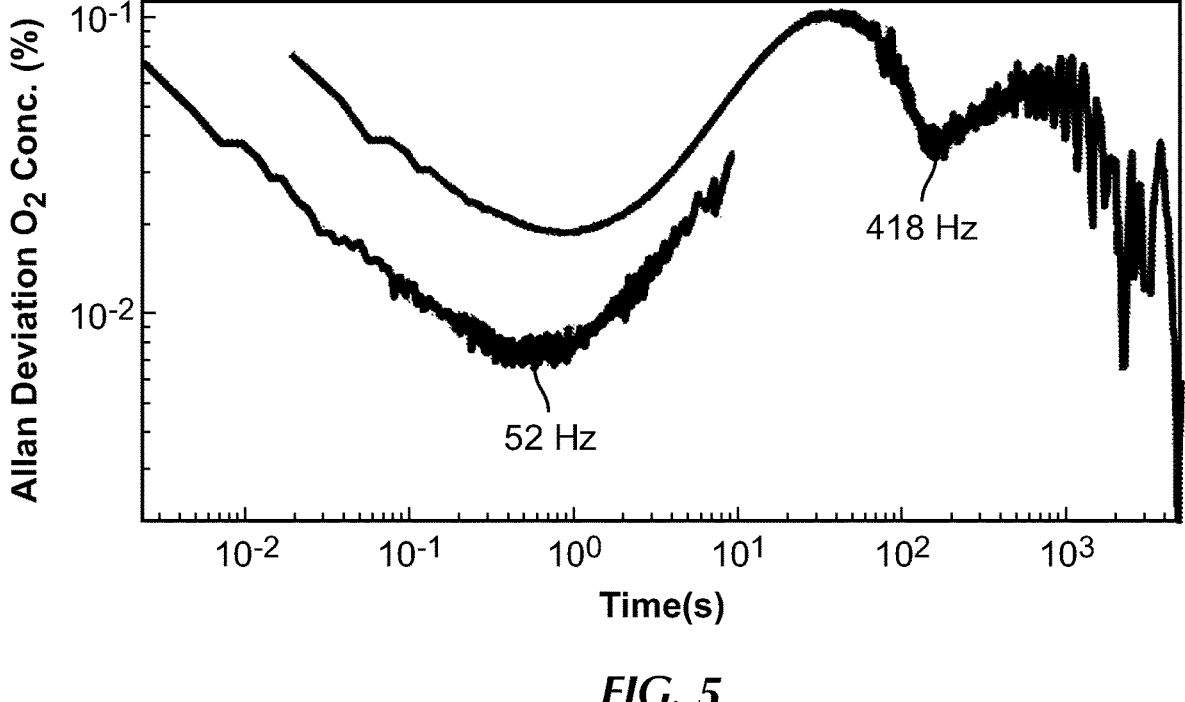
FIG. 5 depicts a graph of an Allan deviation of the on-resonance WMS 2f/1f signal measured with a LIA while locked to the $^{Q}P_5(4)$ transition using the 3-f zero crossing where two update rates are shown for a short and long measurement according to an embodiment of the present invention.

The performance of the final prototype achieves a short-term precision down to ~0.04% $O_2$ at 10 ms averaging time as shown in FIG. 5 (418 Hz line).

In order to provide the desired 10 ms response time the system is optimized for real-time update rate of 418 Hz, however due to memory limitations of the test electronics, this update rate was too high to store large datasets for long-term analysis of system performance. Therefore, in order to investigate long-term drift of the system the update rate was reduced to 52 Hz (while LIA bandwidth was kept unchanged), which allowed for collection of longer time acquisitions for Allan deviation analysis. The measurement is presented in FIG. 5 (52 Hz line). As expected, due to ~8× under-sampling, the short-term precision has been reduced by ~2.8×, but the curve also clearly reveals a sensor drift for averaging times beyond 1 s. The drift has been attributed to a parasitic etalon in the system that will be mitigated in the future by using wedged windows. However, the etalon drift does not cause accuracy issues beyond the target (±1%); therefore, the final sensor performance is within the desired parameter range.

Figure 2B:
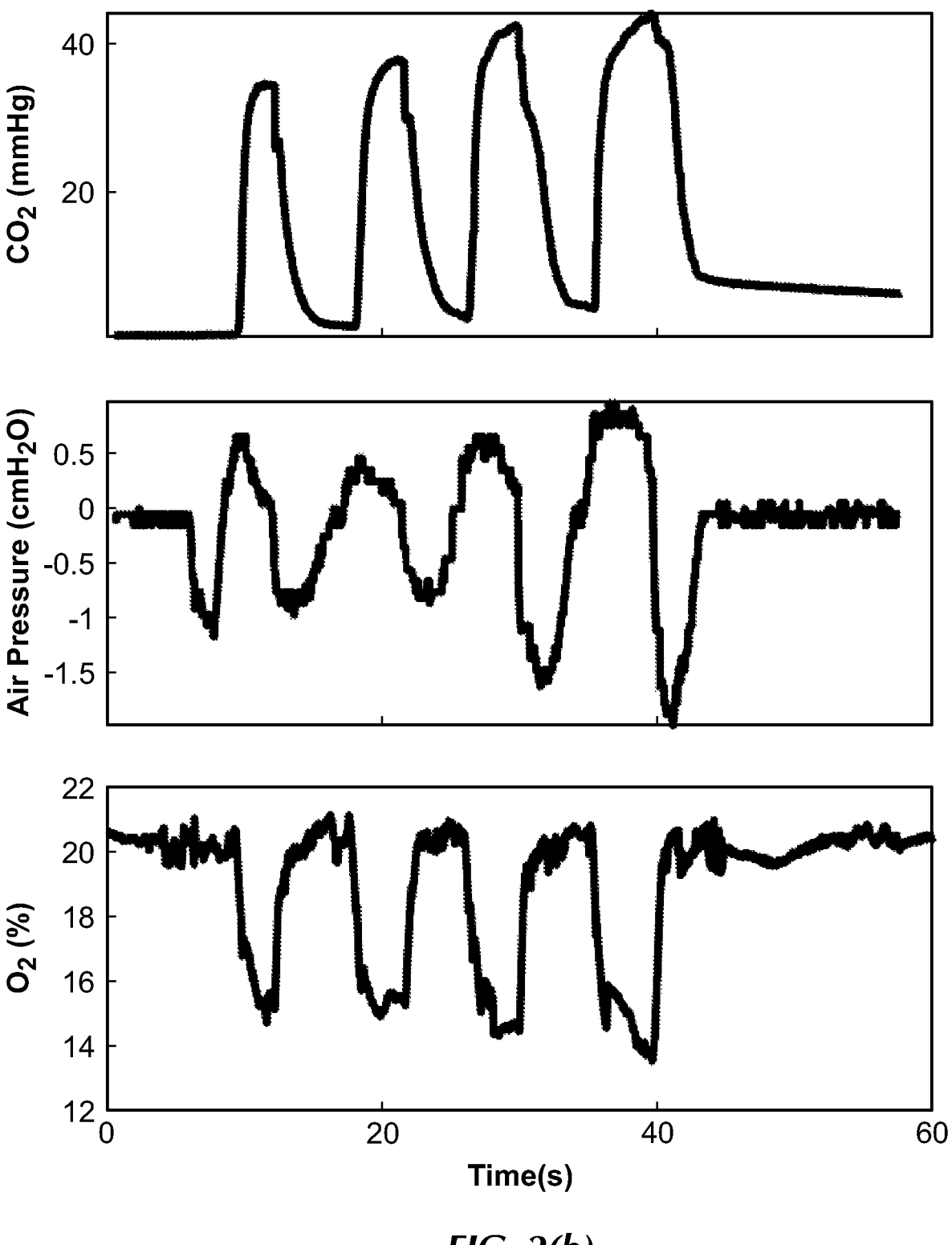
FIG. 2(b) depicts a graph of real-time measurements of patient breathing while monitoring $CO_2$ concentration using commercially available CAPNOSTAT (top), air pressure using Respironics (middle), and $O_2$ concentration using an $O_2$ sensor (bottom) according to an embodiment of the present invention.
Figure 6:
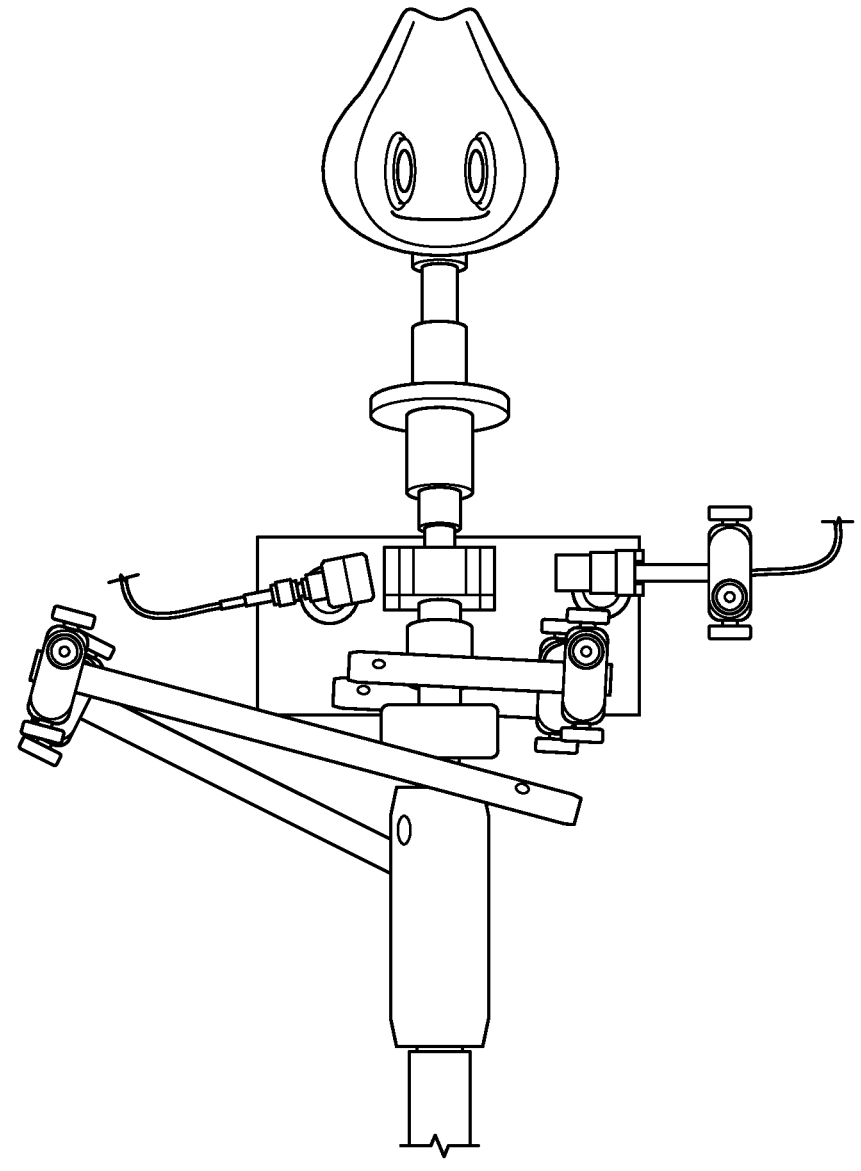
FIG. 6 depicts the $O_2$ sensor head used in conjunction with the CAPNOSTAT 5 for breath measurement.

Lastly, the sensor platform was run simultaneously with commercially available capnograph (CAPNOSTAT 5) that measured $CO_2$ and with an external mouth pressure meter. The $O_2$ sensor was placed upstream of the $CO_2$ sensor and pressure meter as shown in FIG. 6. Then a volunteer breathed into the mask for several breath cycles as shown in FIG. 2. In this example data set the increase in $CO_2$ measured with a commercial capnograph is consistent with increasing $O_2$ consumption as indicated by the $O_2$ trace measured with the sensor described in this invention.

As such, embodiments generally disclosed herein depict a system and method for a novel, small, and lightweight sensor for continuous in-airway monitoring of oxygen at a high sampling rate. The system probes a small volume of exhaled air and can be utilized in a mainstream or sidestream configuration.

It is understood that the above-described embodiments are only illustrative of the application of the principles of the present invention. The present invention may be embodied in other specific forms without departing from its spirit or essential characteristics. All changes that come within the meaning and range of equivalency of the claims are to be embraced within their scope. Thus, while the present invention has been fully described above with particularity and detail in connection with what is presently deemed to be the most practical and preferred embodiment of the invention, it will be apparent to those of ordinary skill in the art that numerous modifications may be made without departing from the principles and concepts of the invention as set forth in the claims.

What is claimed is:

1. A sensing device for measuring oxygen concentration cycles in breath, comprising: a laser configured to emit light at an A-band of oxygen; a lens configured to collimate the light; a multi-pass cell configured to contain a replaceable sample cell, wherein the light passes through the multi-pass cell and is attenuated by oxygen in the replaceable sample cell, the replaceable sample cell comprising a first window between the lens and multi-pass cell and a second window between the multi-pass cell and photodetector; a photodetector configured to convert the attenuated light into an electrical signal; and a lock-in amplifier configured to determine oxygen concentration from a ratio of 1st and 2nd harmonic signal values of the electrical signal, where the lock-in amplifier is further configured to determine a 3rd harmonic signal value that determines a center of oxygen transition for locking a frequency of the laser to the center of the oxygen transition.

2. The sensing device of claim 1, wherein the laser comprises a semiconductor laser.

3. The sensing device of claim 1, wherein the laser is further configured to emit a single frequency radiation coinciding with the A-band of oxygen.

4. The sensing device of claim 1, wherein the first and a second windows are one of anti-reflection coated windows and Brewster angled windows.

5. The sensing device of claim 1, wherein the multi-pass cell comprises a concave mirror at each end configured to fold a path of the light multiple times.

6. The sensing device of claim 1, wherein the laser is further configured to operate in a continuous wave mode at about 760-765 nm.

7. The sensing device of claim 1, wherein the lock-in amplifier is further configured for wavelength modulation spectroscopy.

8. The sensing device of claim 1, wherein the lock-in amplifier is further configured to determine the 1st and 2nd harmonic signal values that determine oxygen concentration from a ratio of the 1st and 2nd harmonic signal values using 2f/f normalization.

9. The sensing device of claim 1, wherein oxygen is measured at a rate of 100 Hz.

10. The sensing device of claim 1, wherein the sample cell is integrated in a replaceable airway adapter to be inserted into the sensing device.

* * * * *